(12) United States Patent
Lai et al.

(10) Patent No.: US 11,033,508 B2
(45) Date of Patent: Jun. 15, 2021

(54) DELAYED SUSTAINED RELEASE PHARMACEUTICAL COMPOSITIONS

(71) Applicant: SpecGX LLC, Webster Groves, MO (US)

(72) Inventors: Tsz Chung Lai, Webster Groves, MO (US); Alexander Brian Lippold, Webster Groves, MO (US); Rebecca Sue Walker, Webster Groves, MO (US); Jae Han Park, Webster Groves, MO (US)

(73) Assignee: SpecGX LLC, Webster Groves, MO (US)

( * ) Notice: Subject to any disclaimer, the term of this patent is extended or adjusted under 35 U.S.C. 154(b) by 0 days.

(21) Appl. No.: 16/002,285

(22) Filed: Jun. 7, 2018

(65) Prior Publication Data

US 2018/0360764 A1    Dec. 20, 2018

Related U.S. Application Data

(60) Provisional application No. 62/519,351, filed on Jun. 14, 2017.

(51) Int. Cl.
| | |
|---|---|
| *A61K 9/50* | (2006.01) |
| *A61K 31/137* | (2006.01) |
| *A61K 9/20* | (2006.01) |
| *A61K 9/48* | (2006.01) |
| *A61K 9/16* | (2006.01) |

(52) U.S. Cl.
CPC .......... *A61K 9/5026* (2013.01); *A61K 9/1623* (2013.01); *A61K 9/1676* (2013.01); *A61K 9/2081* (2013.01); *A61K 9/4808* (2013.01); *A61K 9/5078* (2013.01); *A61K 31/137* (2013.01); *A61K 9/5047* (2013.01)

(58) Field of Classification Search
None
See application file for complete search history.

(56) References Cited

U.S. PATENT DOCUMENTS

| | | | |
|---|---|---|---|
| 6,605,300 B1 | 8/2003 | Burnside | |
| 8,846,100 B2 | 9/2014 | Shojaei | |
| 8,906,413 B2 | 12/2014 | Chang | |
| 9,173,857 B2 | 11/2015 | Shojaei | |
| 2007/0065512 A1* | 3/2007 | Dedhiya | A61K 9/5026 424/469 |
| 2007/0264323 A1* | 11/2007 | Shojaei | A61K 9/1676 424/451 |
| 2014/0271849 A1 | 9/2014 | Raman et al. | |

FOREIGN PATENT DOCUMENTS

WO    20080/231619 A1    12/2018

OTHER PUBLICATIONS

International Search Report and Written Opinion dated Aug. 10, 2018 from related International Application No. PCT/US18/36424, 9 pp.

* cited by examiner

*Primary Examiner* — Susan T Tran

(57) ABSTRACT

Delayed sustained release pharmaceutical compositions that provide therapeutic effects over extended periods of time (i.e., 14-16 hours).

7 Claims, 1 Drawing Sheet

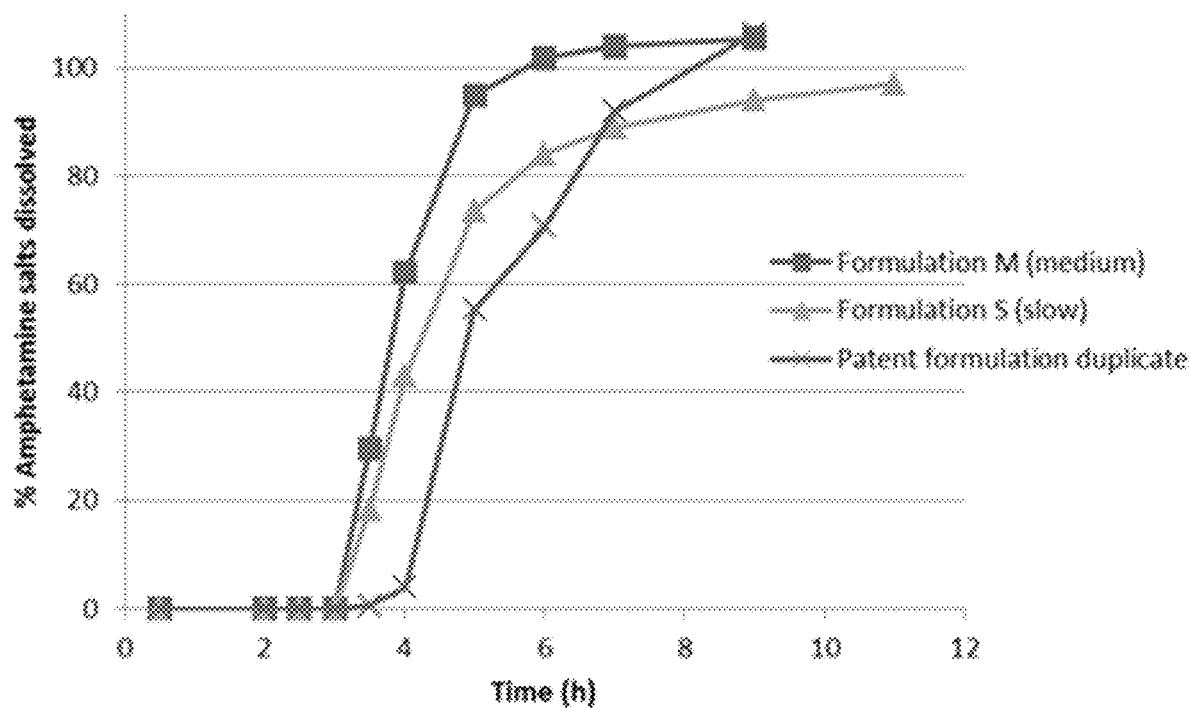

DELAYED SUSTAINED RELEASE PHARMACEUTICAL COMPOSITIONS

CROSS-REFERENCE TO RELATED APPLICATIONS

This application claims the priority of U.S. Provisional Application Ser. No. 62/519,351, filed Jun. 14, 2017, the disclosure of which is hereby incorporated by reference in its entirety.

FIELD OF THE INVENTION

The present disclosure generally relates to long acting pharmaceutical compositions that provide therapeutic effects over extended periods of time (i.e., 14-16 hours).

BACKGROUND OF THE INVENTION

Extended release formulations of mixed amphetamine salts (e.g., ADDERALL® XR) are indicated for the treatment of attention deficit hyperactivity disorder (ADHD). These long acting formulations are designed to provide therapeutic effect up to 12 hours. A portion of the patient population treated with these extended release formulations, however, requires an additional dose of a short-acting immediate release form of amphetamine to achieve clinical benefit beyond 12 hours. The immediate release dose is usually taken 8 to 10 hours after the initial extended release formulation. To achieve a longer acting therapeutic effect (14-16 hours) of amphetamine in ADHD patients by a single dose of medication, a previous method described in U.S. Pat. No. 8,846,100 utilized a multi-particulate drug delivery system consisting of immediate release beads, delayed pulsed release beads, and delayed sustained release beads. The immediate release beads and delayed pulsed release beads are equivalent to ADDERALL® XR, while the delayed sustained release beads extend the therapeutic effect from 12 to 16 hours. Importantly, the delayed sustained release beads must be constructed with a sustained release coating overlaying a delayed enteric release coating, and the coating sequence is critical to achieve the desired (late) $T_{max}$ for meeting the longer-day requirements of therapeutic effect. Thus, there is a need for alternate, once-a-day, long-acting oral formulations of amphetamine salts that provide effective treatment of ADHD for patients with longer day demands (e.g., 14-16 awake hours).

BRIEF DESCRIPTION OF THE DRAWINGS

FIG. 1 presents the in vitro release profiles of Formulation M and Formulation S, and a reference formulation. The pH of the media was pH 1 from 0-2 hours, pH 6 from 2-3 hours, and pH 7.2 from 3-11 hours.

SUMMARY OF THE INVENTION

One aspect of the present disclosure encompasses a delayed sustained release pharmaceutical composition comprising (a) an amphetamine core, the amphetamine core comprising at least one amphetamine salt layered onto or incorporated into an inert core, (b) a sustained release coating layered over the amphetamine core, the sustained release coating comprising at least one sustained release polymer, and (c) a delayed release coating layered over the sustained release coating, the delayed release coating comprising at least one pH-dependent enteric polymer, wherein the delayed sustained release pharmaceutical composition has a d-amphetamine $T_{max}$ of about 7.5 hours to about 9 hours after administration to a human subject.

Another aspect of the present disclosure provides a pharmaceutical composition comprising (a) a plurality of immediate release beads, each immediate release bead comprising at least one amphetamine salt layered onto or incorporated into an inert core, (b) a plurality of delayed release beads, each delayed release bead comprising an amphetamine core and a delayed release coating layered over the amphetamine core, the amphetamine core comprising at least one amphetamine salt layered onto or incorporated into an inert core, and the delayed release coating comprising at least one pH-dependent enteric polymer; and (c) a plurality of delayed sustained release beads, each delayed sustained release bead comprising an amphetamine core, a sustained release coating layered over the amphetamine core, and a delayed release coating layered over the sustained release coating, the amphetamine core comprising at least one amphetamine salt layered onto or incorporated into an inert core, the sustained release coating comprising at least one sustained release polymer, and the delayed release coating comprising at least one pH-dependent enteric polymer, wherein the pharmaceutical composition has a d-amphetamine $T_{max}$ from about 7.9 hours to about 8.8 hours after administration of a 30 mg dose of the pharmaceutical composition to a fasting human subject.

Other aspects and iterations of the disclosure are described in more detail below.

DETAILED DESCRIPTION OF THE INVENTION

The present disclosure provides long acting oral pharmaceutical compositions that provide sustained therapeutic effects over extended periods of time (i.e., 14-16 hours). The multi-phasic drug release profile is achieve by including multiple distinct components in the drug delivery system which are designed to release the drug based on time or physiological pH in the gastrointestinal tract.

(I) Delayed Sustained Release Pharmaceutical Composition

One aspect of the present disclosure provides delayed sustained release pharmaceutical compositions.

(a) Components of the Composition

The delayed sustained release pharmaceutical composition disclosed herein comprises an amphetamine core comprising at least one amphetamine salt layered onto or incorporated into an inert core, a sustained release coating layered over the amphetamine core, and a delayed release coating layered over the sustained release coating.

(i) Amphetamine Core

The amphetamine core comprises at least one amphetamine salt layered onto or incorporated into an inert core.

In general, the amphetamine salt may be dextroamphetamine sulfate, dextroamphetamine saccharate, amphetamine aspartate monohydrate, amphetamine sulfate, or combinations thereof. Other amphetamines and amphetamine salts may be included in the pharmaceutical compositions disclosed herein, for example, other amphetamine salts such as amphetamine hydrochloride, amphetamine hydrogen bromide, and so forth, amphetamine base, chemical and chiral derivatives thereof, and mixtures of any of the foregoing. In one embodiment, the amphetamine salt comprises a mixture dextroamphetamine sulfate, dextroamphetamine saccharate, d,l-amphetamine aspartate monohydrate, and d,l-amphetamine sulfate. The amount of the at least one amphetamine salt can and will vary depending upon the desired dosage of the pharmaceutical composition. In general, the amount of the at least one amphetamine salt present in the pharmaceutical composition may range from about 1 mg to about 100 mg.

The inert core may be a sugar sphere or a non-pareil seed/bead. The inert core may be composed of sucrose, lactose, starch, microcrystalline cellulose, or combinations thereof. In specific embodiments, the inert core may comprise a mixture of sucrose and corn starch. The inert core may have a diameter in the range of about 50 microns to about 1500 microns. In some embodiments, the diameter of the inert core may range from 100 microns to about 1000 microns, or from about 200 microns to about 800 microns. In specific embodiments, the diameter of the inert core may range from about 500 microns to about 600 microns.

In some embodiments, the at least one amphetamine salt may be layered onto the inert core using conventional coating methods. The layer of amphetamine may be present at a coating level of about 10 weight percent to about 25 weight percent of the composition. In specific embodiments, the coating levels of the amphetamine layer may be about 18 weight percent of the composition. The amphetamine layer may further comprise of a binder such as hydroxypropylcellulose, carboxymethylcellulose, hydroxypropyl methylcellulose, or combinations thereof. In specific embodiments, the amphetamine layer may further comprise hydroxypropyl cellulose as a binder. The amount of binder in the amphetamine layer may range from about 15 weight percent to about 25 weight percent of the amphetamine layer. In some embodiments, the amphetamine layer may comprise about 20 weight percent of the amphetamine layer.

In other embodiments, the at least one amphetamine salt may be incorporated into the inert core by forming matrix particles from a mixture comprising the inert material and the at least one amphetamine salt. In still other embodiments, the at least one amphetamine salt may be incorporated into the inert core by soaking the inert core in a solution comprising the at least one amphetamine salt.

(ii) Sustained Release Coating

The delayed sustained release pharmaceutical composition comprises a sustained release coating that is layered over the amphetamine core. The sustained release coating comprises at least one sustained release polymer whose solubility is independent of pH. In general, the sustained release polymer is a water-insoluble or low-water soluble polymer.

Non-limiting examples of suitable sustained release polymers include alkyl alcohols, cellulose acetate, cellulose acetate butyrate, cellulose acetate latex, cellulose acetate propionate, ethyl cellulose, fatty acids, fatty acid esters, hydroxyethyl cellulose, polyvinyl acetate, polyvinyl pyrrolidone, trimethylammonium methyl methacrylate chloride, waxes, co-polymerized ethyl acrylate/methyl methacrylate, co-polymerized ethylacrylate/methyl methacrylate/methacrylic acid with quaternary ammonium groups, ethyl acrylate/methyl methacrylate/methacrylic acid ester with quaternary ammonium groups, and combinations thereof. In specific embodiments, the at least one sustained release polymer may be ethyl cellulose (available under the tradenames SURELEASE® or ETHOCEL™).

The sustained release coating layer may be present at a coating level from of about 5 weight percent to about 8 weight percent of the composition. In various embodiments, the coating level may range from about 6 weight percent to about 7 weight percent of the composition. In one embodiment, the coating level of the sustained release coating may be about 6.5 weight percent of the composition.

In general, the sustained release coating layer completely surrounds or encapsulates the amphetamine core.

(iii) Delayed Release Coating

The delayed sustained release pharmaceutical composition disclosed herein further comprises a delayed release coating layered over the sustained release coating. In general, the delayed release coating comprises at least one a pH-dependent enteric polymer.

Examples of suitable pH-dependent enteric polymers include, without limit, amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer, and combinations thereof. In specific embodiments, the at least one pH-dependent enteric polymer may be a copolymer of methacrylic acid, methyl methacrylate, and methyl acrylate (available under the tradename EUDRAGIT® FS 30 D). The copolymer of methacrylic acid, methyl methacrylate, and methyl acrylate undergoes dissolution at pH values above pH 7.0.

The delayed release coating layer may be present at a coating level from about 30 weight percent to about 45 weight percent of the composition. In certain embodiments, the coating level of the delayed release coating may range from about 35 weight percent to about 40 weight percent of the composition. In specific embodiments, the coating level of the delayed release coating may be about 37.5 weight percent of the composition.

The delayed release coating layer may further comprise an excipient. In some embodiments, the excipient may be magnesium silicate or talc. The magnesium silicate or talc may function as anti-caking agent, filler, lubricant, or glidant in the pharmaceutical compositions disclosed herein.

In general, the delayed release coating layer completely surrounds or encapsulates the sustained release coating layer.

(iv) Optional Film Coatings

In certain embodiments, the amphetamine core, the sustained release coating layer, and/or the delayed release coating layer may further be coated with an optional film coating. The film coating may provide moisture protection, enhanced appearance, and/or increased mechanical integrity. The film coating does not affect the rate of release of the at least one amphetamine salt.

Film coatings are known the art, e.g., some are commercially available under the tradename OPADRY®. Typically, a film coating comprises at least one water-soluble polymer and at least one plasticizer. Non-limiting examples of suitable polymers include hydroxypropylmethyl cellulose, hydroxypropyl cellulose, hydroxypropylethyl cellulose, ethyl cellulose, methyl cellulose, cellulose acetate phthalate, microcrystalline cellulose and carrageenan, acrylic polymers, polyvinyl alcohol, anionic and cationic polymers of methacrylic acid, copolymers of methacrylates, copolymers of acrylates and methacrylates, copolymers of ethacrylate and methyl methacrylate, polyvinylacetate phthalate, and shellac. Examples of suitable plasticizers include, without limit, triethyl citrate (TEC), acetyltriethyl citrate (ATEC), acetyl tri-n-butyl citrate (ATBC), dibutyl sebacate, diethyl phthalate, and triacetin. The film coating may optionally comprise additional agents such as coloring agents, fillers, flavoring agents, taste-masking agents, surfactants, antitacking agents, and/or anti-foaming agents. Suitable examples of these agents are well known in the art.

(b) Properties of the Composition

The delayed sustained release pharmaceutical composition disclosed herein exhibits pH-dependent and sustained release of the at least one amphetamine salt. The pH-dependent release of the at least one amphetamine salt occurs at pH levels above 7.0. Thus, there is no release of the at least one amphetamine salt until the composition enters the distal gastrointestinal tract (i.e., jejunum, ileum, and colon) where the pH ranges from about 7.0 to 8.5. Once release is initiated, the at least one amphetamine salt is released over a period of about 2 hours, about 3 hours, about 4 hours, about 5 hours, or about 6 hours.

In one embodiment, the delayed sustained release pharmaceutical composition has a d-amphetamine $T_{max}$ of about 7.5 hours to about 9 hours after administration to a human subject. In one embodiment, the delayed sustained release pharmaceutical composition has a d-amphetamine $T_{max}$ of about 7.9 hours after administration to a human subject. In one embodiment, the delayed sustained release pharmaceutical composition has a d-amphetamine $T_{max}$ of about 8.8 hours after administration to a human subject.

II. Three Bead Pharmaceutical Composition

Another aspect of the present disclosure encompasses a pharmaceutical composition comprising a plurality of immediate release beads, a plurality of delayed release beads, and plurality of delayed sustained release beads.

(a) Immediate Release Beads

Each of the plurality of immediate release beads comprises at least one amphetamine salt layered onto or incorporated into an inert core.

In general, the amphetamine salt may be dextroamphetamine sulfate, dextroamphetamine saccharate, amphetamine aspartate monohydrate, amphetamine sulfate, or combinations thereof. Other amphetamines and amphetamine salts may be included in the pharmaceutical compositions disclosed herein, for example, other amphetamine salts such as amphetamine hydrochloride, amphetamine hydrogen bromide, and so forth, amphetamine base, chemical and chiral derivatives thereof, and mixtures of any of the foregoing. In one embodiment, the amphetamine salt comprises a mixture dextroamphetamine sulfate, dextroamphetamine saccharate, d,l-amphetamine aspartate monohydrate, and d,l-amphetamine sulfate.

The inert core may be a sugar sphere or a non-pareil seed/bead. The inert core may be composed of sucrose, lactose, starch, microcrystalline cellulose, or combinations thereof. In specific embodiments, the inert core may comprise a mixture of sucrose and corn starch. The inert core may have a diameter in the range of about 50 microns to about 1500 microns. In some embodiments, the diameter of the inert core may range from 100 microns to about 1000 microns, or from about 200 microns to about 800 microns. In specific embodiments, the diameter of the inert core may range from about 500 microns to about 600 microns.

In some embodiments, the at least one amphetamine salt may be layered onto the inert core using conventional coating methods. The layer of amphetamine may be present at a coating level of about 10 weight percent to about 25 weight percent of the bead. In one embodiment, the coating level of the amphetamine layer may be about 18 weight percent of the bead. The amphetamine layer may further comprise from of a binder such as hydroxypropylcellulose, carboxymethylcellulose, hydroxypropyl methylcellulose, and combinations thereof. In specific embodiments, the amphetamine layer may further comprise hydroxypropyl cellulose as a binder. The amount of binder in the amphetamine layer may range from about 15 weight percent to about 25 weight percent of the amphetamine layer. In some embodiments, the amphetamine layer may comprise from about 20 weight percent of the binder.

In other embodiments, the at least one amphetamine salt may be incorporated into the inert core by forming particles from a mixture comprising the inert material and the at least one amphetamine salt. In still other embodiments, the at least one amphetamine salt may be incorporated into the inert core by soaking the inert core in a solution comprising the at least one amphetamine salt.

In some embodiments, the layer of amphetamine may be coated with a film coating as described above in section (I)(a)(iv).

(b) Delayed Release Beads

Each of the plurality of the delayed release beads comprises an amphetamine core and a delayed release coating layered over the amphetamine core.

(i) Amphetamine Core

The amphetamine core comprises at least one amphetamine salt layered onto or incorporated into an inert core. Stated another way, the amphetamine core is essentially an immediate release bead, which is described above in section (II)(a).

(ii) Delayed Release Coating of Delayed Release Beads

The delayed release coating that is layered over the amphetamine core comprises at least one pH-dependent enteric polymer. Examples of suitable pH-dependent enteric polymers include, without limit, amylose acetate phthalate, cellulose acetate phthalate, cellulose acetate succinate, cellulose acetate trimellitate, carboxymethyl ethylcellulose, co-polymerized methacrylic acid/acrylic acid ethyl esters, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer, and combinations thereof. In specific embodiments, the at least one pH-dependent enteric polymer may be a copolymer of methacrylic acid and ethyl acrylate (available under the tradename EUDRAGIT® L 30 D-55). The copolymer of methacrylic acid and ethyl acrylate undergoes dissolution at pH values above pH 5.5.

The delayed release coating layer of the delayed release beads may be present at a coating level from about 20 weight percent to about 35 weight percent of the bead. In certain embodiments, the coating level of the delayed release coating may be about 25 weight percent to about 30 weight percent of the bead. In specific embodiments, the coating level of the delayed release coating may be about 27 weight percent of the bead.

The delayed release coating layer of the delayed release beads may further comprise at least one excipient. In some embodiments, the delayed release coating may further comprise a plasticizer. Examples of suitable plasticizers include, without limit, triethyl citrate (TEC), acetyltriethyl citrate (ATEC), acetyl tri-n-butyl citrate (ATBC), dibutyl sebacate, diethyl phthalate, and triacetin. In other embodiments, the delayed release coating may further magnesium silicate or talc (which functions as anti-caking agent, filler, lubricant, or glidant). In some embodiments, the delayed release coating may further comprise TEC and talc.

In general, the delayed release coating layer completely surrounds or encapsulates the amphetamine core.

In some embodiments, the delayed release coating may be coated with a film coating essentially as described above in section (I)(a)(iv).

(c) Delayed Sustained Release Beads

Each of the delayed sustained release beads comprises an amphetamine core, a sustained release coating layered over the amphetamine core, and a delayed release coating layered over the sustained release coating.

(i) Amphetamine Core

The amphetamine core comprises at least one amphetamine salt layered onto or incorporated into an inert core. Stated another way, the amphetamine core is essentially an immediate release bead, which is described above in section (II)(a).

(ii) Sustained Release Coating of Delayed Sustained Release Beads

The sustained release coating comprises at least one sustained release polymer whose solubility is independent of pH. In general, the sustained release polymer is a water-insoluble or low-water soluble polymer.

Non-limiting examples of suitable sustained release polymers include alkyl alcohols, cellulose acetate, cellulose acetate butyrate, cellulose acetate latex, cellulose acetate propionate, ethyl cellulose, fatty acids, fatty acid esters, hydroxyethyl cellulose, polyvinyl acetate, polyvinyl pyrrolidone, trimethylammonium methyl methacrylate chloride, waxes, co-polymerized ethyl acrylate/methyl methacrylate, co-polymerized ethylacrylate/methyl methacrylate/methacrylic acid with quaternary ammonium groups, ethyl acrylate/methyl methacrylate/methacrylic acid ester with quaternary ammonium groups, and combinations thereof. In specific embodiments, the sustained release polymer may be ethyl cellulose (available under the tradenames SURELEASE® or ETHOCEL™).

The sustained release coating layer may be present at a coating level from of about 4 weight percent to about 10 weight percent of the bead. In various embodiments, the coating level of the sustained release coating may be about 5 weight percent to about 9 weight percent of the bead. In one embodiment, the coating level of the sustained release coating may be about 6 weight percent of the bead. In another embodiment, the coating level of the sustained release coating may be about 8 weight percent of the bead.

In general, the sustained release coating layer completely surrounds or encapsulates the amphetamine core.

In some embodiments, the sustained release coating may be coated with a film coating essentially as described above in section (I)(a)(iv).

(iii) Delayed Release Coating of Delayed Sustained Release Beads

The outer layer of the delayed sustained release beads comprises a delayed release coating, which comprises at least one pH-dependent enteric polymer.

Examples of suitable pH-dependent enteric polymers include, without limit, amylose acetate phthalate, cellulose acetate phthalate, cellulose acetate succinate, cellulose acetate trimellitate, carboxymethyl ethylcellulose, co-polymerized methacrylic acid/methacrylic acid methyl esters, co-polymerized methacrylic acid/methyl methacrylate, co-polymerized methylacrylate/methyl methacrylate/methacrylic acid, hydroxypropyl methylcellulose acetate succinate, hydroxypropyl methylcellulose phthalate, polyvinyl acetate phthalate, styrene maleic acid copolymer, styrene vinylpyridine copolymer, and combinations thereof. In specific embodiments, the at least one pH-dependent enteric polymer may be a copolymer of methacrylic acid, methyl methacrylate, and methyl acrylate (available under the tradename EUDRAGIT® FS 30 D). The copolymer of methacrylic acid, methyl methacrylate, and methyl acrylate undergoes dissolution at pH values above pH 7.0.

The delayed release coating layer may be present at a coating level from about 15 weight percent to about 30 weight percent of the bead. In certain embodiments, the coating level of the delayed release coating may range from about 20 weight percent to about 25 weight percent of the bead. In specific embodiments, the coating level of the delayed release coating may be about 22 weight percent of the bead.

The delayed release coating layer may further comprise an excipient. In some embodiments, the excipient may be magnesium silicate or talc. The magnesium silicate or talc may function as anti-caking agent, filler, lubricant, or glidant in the pharmaceutical compositions disclosed herein.

In general, the delayed release coating layer completely surrounds or encapsulates the sustained release coating layer.

In some embodiments, the delayed release coating may be coated with a film coating essentially as described above in section (I)(a)(iv).

(d) Dosage Forms

The plurality of immediate release beads, the plurality of delayed release beads, and the plurality of delayed sustained release beads may be formulated in a variety of dosage forms. In general, the dosage forms are for oral administration. In one embodiment, the pluralities of immediate release beads, delayed release beads, and delayed sustained release beads may be incorporated into a capsule. The shell of the capsule may comprise gelatin, hydrolyzed starch, or a polymer such as hydroxypropylmethylcellulose. In other embodiments, the pluralities of immediate release beads, delayed release beads, and delayed sustained release beads may be incorporated into a tablet. The tablet may be compressed, compacted, molded, or layered. Such dosage forms may be prepared using conventional methods known to those in the field of pharmaceutical formulation and described in pertinent texts, e.g., in Gennaro, A. R., editor. "Remington: The Science & Practice of Pharmacy", 21st ed., 2006, Williams & Williams, and in the "Physician's Desk Reference", 66th ed., 2014, PDR Staff.

In general, the dose of the at least one amphetamine salt is equally distributed among the pluralities of immediate release beads, delayed release beads, and delayed sustained release beads. That is, each of the pluralities of immediate release beads, delayed release beads, and delayed sustained release beads comprises 33.3% by weight of the at least one amphetamine salt.

(e) Pharmacokinetic Properties

Measures of bioavailability well known in the art include the area under the plasma concentration-time curve (AUC), the concentration maximum ($C_{max}$), and the time to $C_{max}$ (i.e., $T_{max}$). For example, see Remington: The Science and Practice of Pharmacy, 2006, supra.

AUC is a measurement of the area under the plasma concentration-time curve, and is representative of the amount of drug absorbed following administration of a single dose of a drug.

$C_{max}$ is the maximum plasma concentration achieved after oral drug administration. An oral drug administration results in one $C_{max}$, but may result in greater than one "peak plasma concentration" or "plasma concentration peak" (for example, following the administration of a pulsed dose formulation).

$T_{max}$ is the amount of time necessary to achieve the $C_{max}$ after oral drug administration, and is related to the rate of absorption of a drug.

Half-life ($t_{1/2}$) is the period of time required for the concentration or amount of drug in the body to be reduced by one-half.

The elimination rate ($K_{el}$) is the fraction of drug that is eliminated per unit of time.

Bioequivalence is the absence of a significantly different rate and extent of absorption in the availability of the active ingredient when administered at the same dose under similar conditions. Bioequivalence can be measured by pharmacokinetic parameters such as, for example, AUC and $C_{max}$.

In some embodiments, the pharmaceutical composition may have a d-amphetamine $T_{max}$ from about 7.9 hours to about 8.8 hours, a d-amphetamine $C_{max}$ from about 41 ng/ml to about 44 ng/mL, a d-amphetamine $AUC_{inf}$ from about 884 ng·h/mL to about 934 ng·h/mL after administration of a 30 mg dose of the pharmaceutical composition to a fasting human subject. The $t_{1/2}$ may range from about 10.7 to about 11.1 hours, and the $K_{el}$ ($h^{-1}$) may range from about 0.06 to about 0.08.

(III) Processes for Preparing the Compositions

The pharmaceutical composition disclosed herein may be prepared using standard coating processes such as, spray coating, Wurster coating, fluidized bed coating, and the like). Additional guidance can be found, for example, in K. Masters, *Spray Drying Handbook*, $4^{th}$ edition, Halsted Press, 1985.

Definitions

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about," particularly in reference to a given quantity, is meant to encompass deviations of plus or minus five percent.

The term "enteric polymer" is used herein to represent a polymer, whose solubility is dependent on the pH in such a manner that it generally prevents the release of the drug in the stomach but permits the release of the drug at some stage after the formulation has emptied from the stomach.

The term "sustained release polymer" refers to a polymer whose solubility is independent of pH.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Three Bead Formulation

Two formulations (medium, M, and slow, S) of a three bead composition comprising immediate release (IR) beads, delayed or extended release (ER) beads, and delayed sustained release (DSR) beads were prepared. The components of each formulation are listed in Table 1 below.

TABLE 1

Components of Three Bead Compositions

| | | % (w/w) | |
| --- | --- | --- | --- |
| Bead | Component | Formulation M (Medium) | Formulation S (Slow) |
| IR Beads | Sugar spheres 30/35 | 87.50 | 87.50 |
| | Amphetamine sulfate | 2.50 | 2.50 |
| | Amphetamine aspartate | 2.50 | 2.50 |
| | Dextroamphetamine sulfate | 2.50 | 2.50 |
| | Dextroamphetamine saccharate | 2.50 | 2.50 |
| | Klucel EF | 2.50 | 2.50 |
| | Total | 100.00 | 100.00 |
| ER Beads | IR beads | 62.50 | 62.50 |
| | Eudragit L 30 D-55 | 26.79 | 26.79 |
| | TEC | 2.68 | 2.68 |
| | Talc | 8.04 | 8.04 |
| | Total | 100.00 | 100.00 |
| DSR Beads | IR Beads | 60.06 | 58.48 |
| | $1^{st}$ Coat - Surelease E-7-19040 | 6.61 | 8.19 |
| | $2^{nd}$ Coat - Eudragit FS 30 D | 22.23 | 22.23 |
| | $2^{nd}$ Coat - Talc | 11.10 | 11.10 |
| | Total | 100.00 | 100.00 |

Coating dispersions were prepared by mixing the appropriate components in a suitable solvent, and the dispersions were sprayed into the appropriate beads.

Example 2

In Vitro Release

Release of amphetamine from each of the formulation prepared in Example 1 was measured using an in vitro release assay and compared to that of a reference formulation (i.e., Adderall® XR). Release was measured at pH 1.0 for the hours 0-2, pH 6.0 for hours 2-3, and pH 7.2 for hours 3-11 of the assay. The dissolution profiles are presented in FIG. 1.

Example 3

Pharmacokinetic Study

A fasted, human pharmacokinetic study was conducted to compare the pharmacokinetic profiles of 30 mg strength capsules comprising Formulations M, S, and a reference (i.e., Adderall® XR+IR amphetamine). The results are presented in Tables 2 and 3.

TABLE 2

Comparisons of plasma PK parameters for d-amphetamine

| PK Parameter | Formulation M | | Formulation S | | Reference | |
| --- | --- | --- | --- | --- | --- | --- |
| | Ratio % (M/Ref) | 90% CI | Ratio % (S/Ref) | 90% CI | Ratio % | 90% CI |
| $C_{max}$ (ng/mL) | 116.9 | (111.8, 122.2) | 111.8 | (107.4, 116.9) | 101.0 | (96.9, 105.3) |
| $AUC_{inf}$ (ng · h/mL) | 104.7 | (100.5, 109.2) | 102.3 | (98.2, 106.6) | 104.4 | (100.3, 108.7) |

TABLE 3

Comparisons of plasma PK parameters for d-amphetamine

| PK Parameter | Formulation M | Formulation S | Normalized SHP465 results* |
| --- | --- | --- | --- |
| $T_{max}$ (h) | 7.9 | 8.8 | 7 |
| $C_{max}$ (ng/mL) | 43.7 | 41.6 | 43.4 |
| $AUC_{inf}$ (ng · h/mL) | 933.6 | 884.9 | 953.7 |
| $t_{1/2}$ (h) | 11.1 | 10.7 | 10.9 |
| $k_{el}$ (h$^{-1}$) | 0.06 | 0.07 | 0.07 |

*SHP results were normalized from the PK results of 50 mg strength in U.S. Pat. No. 8,846,100.

Highly comparable pharmacokinetic profiles were found between the reference and Formulation M and S prepared using the coating sequence as described herein. The 90% CIs of all pharmacokinetic parameters are within limits of 80-125%, showing bioequivalence to the reference.

What is claimed is:

1. A pharmaceutical composition consisting of:
   a plurality of immediate release beads, each immediate release bead consisting of an amphetamine core, wherein the amphetamine core consists of at least one amphetamine salt and an optional binder layered onto or incorporated into an inert core;
   a plurality of delayed release beads, each delayed release bead consisting of an immediate release bead and a delayed release coating layered thereover, wherein the delayed release coating consists of a copolymer of methacrylic acid and ethyl acrylate and an optional excipient, and is present at a coating level of about 25% to about 30% by weight of the bead; and
   a plurality of delayed sustained release beads, each delayed sustained release bead consisting of an immediate release bead, a sustained release coating layered over the immediate release bead, and a delayed release coating layered over the sustained release coating, wherein the sustained release coating consists of ethyl cellulose and is present at a coating level from about 5% to about 9% by weight of the bead, and the delayed release coating consists a copolymer of methacrylic acid, methyl methacrylate, and methyl acrylate and an optional excipient, and is present at a coating level from about 20% to about 25% by weight of the bead;
   wherein the pharmaceutical composition has a d-amphetamine $T_{max}$ from 7.9 hours to 8.8 hours after administration of a 30 mg dose of the pharmaceutical composition to a fasting human subject.

2. The pharmaceutical composition of claim 1, wherein the at least one amphetamine salt is dextroamphetamine sulfate, dextroamphetamine saccharate, amphetamine aspartate monohydrate, amphetamine sulfate, or mixtures thereof, and the at least one amphetamine salt is present in the pharmaceutical composition in an amount from 12.5 mg to 75 mg.

3. The pharmaceutical composition of claim 1, wherein the pharmaceutical composition has a d-amphetamine $C_{max}$ from about 41 ng/ml to about 44 ng/mL, and a d-amphetamine $AUC_{inf}$ from about 884 ng·h/mL to about 934 ng·h/mL after administration of a 30 mg dose of the pharmaceutical composition to a fasting human subject.

4. The pharmaceutical composition of claim 1, wherein the pluralities of immediate release beads, delayed release beads, and delayed sustained release beads are incorporated into a capsule.

5. The pharmaceutical composition of claim 1, wherein the pluralities of immediate release beads, delayed release beads, and delayed sustained release beads are incorporated into a tablet.

6. The pharmaceutical composition of claim 1, wherein each of the pluralities of immediate release beads, delayed release beads, and delayed sustained release beads comprises 33.3% by weight of the at least one amphetamine salt.

7. A method for treating for treating attention deficit hyperactivity disorder (ADHD), the method comprises administering to a patient in need thereof the pharmaceutical composition of claim 1.

* * * * *